(12) United States Patent
Mann et al.

(10) Patent No.: US 8,248,614 B2
(45) Date of Patent: Aug. 21, 2012

(54) QUANTITATIVE PHASE-IMAGING SYSTEMS

(75) Inventors: Christopher J. Mann, Knoxville, TN (US); Philip R. Bingham, Knoxville, TN (US); Shaun S. Gleason, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 492 days.

(21) Appl. No.: 12/405,063

(22) Filed: Mar. 16, 2009

(65) Prior Publication Data
US 2010/0231895 A1 Sep. 16, 2010

(51) Int. Cl.
*G01B 9/02* (2006.01)
(52) U.S. Cl. .................................................. 356/485
(58) Field of Classification Search .................. 356/456, 356/489, 496, 511, 503, 504, 512, 485
See application file for complete search history.

(56) References Cited

U.S. PATENT DOCUMENTS

| | | | |
|---|---|---|---|
| 4,453,827 A | 6/1984 | Taboada | |
| 4,701,006 A | 10/1987 | Perlmutter | |
| 5,418,797 A | 5/1995 | Bashkansky et al. | |
| 6,002,480 A * | 12/1999 | Izatt et al. | 356/479 |
| RE36,529 E * | 1/2000 | Lewis et al. | 356/456 |
| 6,760,134 B1 | 7/2004 | Schilling et al. | |
| 6,809,814 B2 | 10/2004 | Xie et al. | |
| 6,809,845 B1 | 10/2004 | Kim et al. | |
| 6,943,924 B2 | 9/2005 | Marquet et al. | |
| 7,127,109 B1 | 10/2006 | Kim | |
| 7,312,875 B2 | 12/2007 | Hanson et al. | |
| 7,364,296 B2 | 4/2008 | Miller et al. | |
| 7,978,336 B2 | 7/2011 | Mann et al. | |
| 7,990,524 B2 * | 8/2011 | Jureller et al. | 356/36 |
| 2008/0287929 A1 * | 11/2008 | Holliday et al. | 606/5 |
| 2008/0304046 A1 * | 12/2008 | Lee et al. | 356/51 |

OTHER PUBLICATIONS

Goodman, J. W., *Introduction to Fourier Optics*. 2ed. McGraw-Hill, New York, New York, Copyright 1996, 456 pages.
Schnars, U. et al., "Direct recording of holograms by a CCD target and numerical reconstruction," *Applied Optics*, vol. 33, No. 2, 1994, pp. 179-181.
Török, P. et al., *Optical Imaging and Microscopy: Techniques and Advanced Systems*, Springer, Berlin, Germany, Copyright 2003, 405 pages.
Warnasooriya, N. et al., "LED-based multi-wavelength phase imaging interference microscopy," *Optics Express*, vol. 15, No. 15, 2007, pp. 9239-9247.
Yamauchi, T., "Low-coherent quantitative phase microscope for nanometer-scale measurement of living cells morphology," *Optics Express*, vol. 16, No. 16, 2008, pp. 12227-12238.

(Continued)

*Primary Examiner* — Michael A Lyons
*Assistant Examiner* — Jonathan Hansen
(74) *Attorney, Agent, or Firm* — Brinker Hofer Gilson & Lione

(57) ABSTRACT

An optical system performs imaging in a transmissive and reflective mode. The system includes an optical interferometer that generates interference phenomena between optical waves to measure multiple distances, thicknesses, and indices of refraction of a sample. Measurements are made through a galvanometer that scans a pre-programmed angular arc. An excitation-emission device allows an electromagnetic excitation and emission to pass through an objective in optical communication with the sample. An electromagnetic detector receives the output of the optical interferometer and the excitation-emission device to render a magnified three dimensional image of the sample.

23 Claims, 5 Drawing Sheets

OTHER PUBLICATIONS

Yu, L. et al., "Improved tomographic imaging of wavelength scanning digital holographic microscopy by use of digital spectral shaping," *Optics Express*, vol. 15, No. 3, 2007, pp. 878-886.

Yu, L. et al., "Wavelength scanning digital interference holography for variable tomographic scanning," *Optics Express*, vol. 13, No. 15, 2005, pp. 5621-5627.

Yamaguchi, Ichirou et al.; "Phase-shifting color digital holography";Optics Letters, vol. 27, No. 13; Jul. 1, 2002; pp. 1108-1110.

Bachim, B. L. et al., "Microinterferometric optical phase tomography for measuring small, asymmetric refractive-index differences in the profiles of optical fibers and fiber devices," *Applied Optics*, vol. 44, No. 3, 2005, pp. 316-327.

Beuthan, J. et al., "The spatial variation of the refractive index in biological cells," *Phys. Med. Biol.*, vol. 41, 1996, pp. 369-382.

Charrière, F. et al., "Living specimen tomography by digital holographic microscopy: morphometry of testate amoeba," *Optics Express*, vol. 14, No. 16, 2006, pp. 7005-7013.

Choi, W. et al., "Extended depth of focus in tomographic phase microscopy using a propogation algorithm," *Optics Letters*, vol. 33, No. 2, 2008, pp. 171-173.

Cuche, E. et al., "Digital holography for quantitative phase-contrast imaging," *Optics Letters*, vol. 24, No. 5, 1999, pp. 291-293.

Ferraro, P. et al., "Quantitative phase-contrast microscopy by a lateral shear approach to digital holographic image reconstruction," *Optics Letters*, vol. 31, No. 10, 2006, pp. 1405-1407.

Ferraro, P. et al., "Quantitative Phase Microscopy of microstructures with extended measurement range and correction of chromatic aberrations by multiwavelength digital holography," *Optics Express*, vol. 15, No. 22, 2007, pp. 14591-14600.

Goodman, J. W. et al., "Digital Image Formation form Electronically Detected Holograms," *Applied Physics Letters*, vol. 11, No. 3, 1967, pp. 77-79.

Grilli, S. et al., "Whole optical wavefields reconstruction by Digital Holography," *Optics Express*, vol. 9, No. 6, 2001, pp. 294-302.

Huntley, J. M. et al., "Temporal phase-unwrapping algorithm for automated interferogram analysis," *Applied Optics*, vol. 32, No. 17, 1993, pp. 3047-3052.

Iwai, H. et al., "Quantitative phase imaging using actively stabilized phase-shifting low-coherence interferometry," *Optics Letters*, vol. 29, No. 20, 2004, pp. 2399-2401.

Kim, M. K. et al., Chapter 2, "Digital Holography and Multi-Wavelength Interference Techniques," *Digital Holography and Three-Dimensional Display: Principles and Applications*, Springer, New York, New York, Copyright 2006, pp. 51-72.

Kühn, J. et al., "Real-time dual-wavelength digital holographic microscopy with a single hologram acquisition," *Optics Express*, vol. 15, No. 12, 2007, pp. 7231-7242.

Lo, C. F., "Surface normal guided method for two-dimensional phase unwrapping," *Optik*, vol. 113, No. 10, 2002, pp. 439-447.

Lue, N. et al., "Quantitative phase imaging of live cells using fast Fourier phase microscopy," *Applied Optics*, vol. 46, No. 10, 2007, pp. 1836-1842.

Mann, C. J. et al., "High-resolution quantitative phase-contrast microscopy by digital holography," *Optics Express*, vol. 13, No. 22, 2005, pp. 8693-8698.

Mann, C. J. et al., "Movies of cellular and sub-cellular motion by digital holographic microscopy," *BioMedical Engineering OnLine*, vol. 5, 2006, pp. 1-10.

Mann, C. J. et al., "Quantitative phase imaging by three-wavelength digital holography," *Optics Express*, vol. 16, No. 13, 2008, pp. 9753-9764.

Park, Y. et al., "Diffraction phase and fluorescence microscopy," *Optics Express*, vol. 14, No. 18, pp. 8263-8268, Sep. 4, 2006.

\* cited by examiner

QUANTITATIVE PHASE-IMAGING SYSTEMS

RELATED APPLICATION

This application is related to U.S. application Ser. No. 12/405,089 filed on Mar. 16, 2009, entitled "Quantitative Phase-Contrast and Excitation-Emission Systems" and U.S. application Ser. No. 12/381,758 filed on Mar. 16, 2009, entitled "Three Wavelength Quantitative Imaging Systems," which are incorporated by reference.

BACKGROUND OF THE INVENTION

1. Technical Field

This disclosure relates to optical systems and particularly to systems that generate three-dimensional visual images.

2. Related Art

The need for accurate and full-field measurements of objects in life sciences is increasing. Magnified views of living organisms may promote diagnostics, treatment, and prevention of disease of the body and mind. Full-field views promote many branches of science including anthropology and ecology that study the organisms' life processes, relationships, and environment.

Unfortunately, the length, width, and depth of an object are measured by some systems through the physical rotation of the object. The system may require complex mechanical translations that may invade the object and require long acquisition times of several views to render a less than clear image at a limited resolution.

SUMMARY

An optical system performs imaging in a transmissive and reflective mode. The system includes an optical interferometer that generates interference phenomena between optical waves to measure multiple distances, thicknesses, and indices of refraction of a sample. Measurements are made through a galvanometer that scans a pre-programmed angular arc. An excitation-emission device allows an electromagnetic excitation and emission to pass through an objective in optical communication with the sample. An electromagnetic detector receives the output of the optical interferometer and the excitation-emission device to render a magnified three dimensional image of the sample.

Other systems, methods, features, and advantages, will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The system may be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

Figure 1:
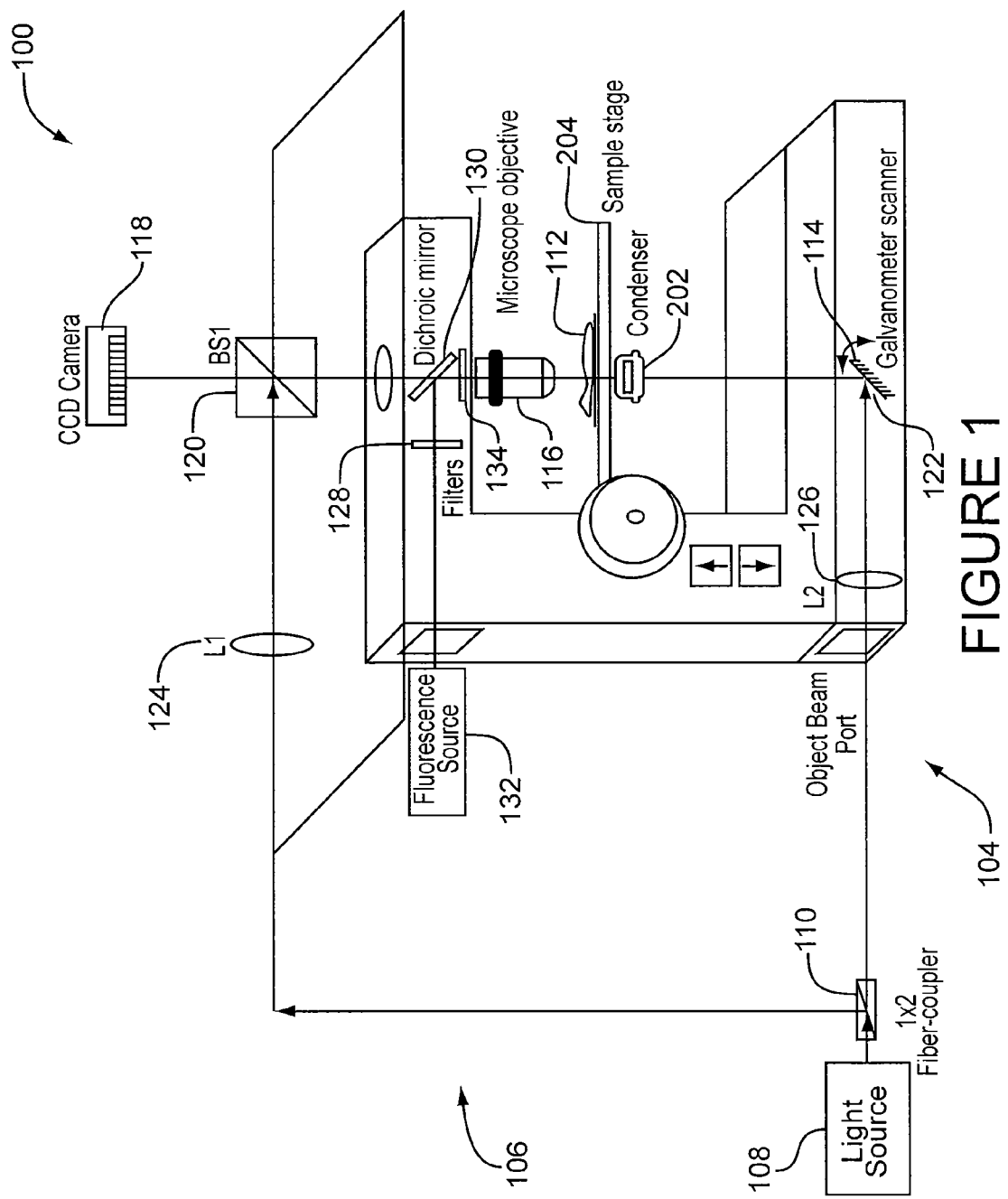
FIG. 1 is a single wavelength optical interferometer and excitation-emission device.

Quantifying optical path length changes may detect refractive indexes or optical thickness variations with a vertical and horizontal resolution of a few nanometers. The quantification may be used to investigate morphological variations associated with dynamic anthropologic processes, ecologic processes, and biological processes including drug delivery, disease progression, and/or other pathological or scientific occurrences.

An optical system may include one or more digital optical interferometers that may not require multiple image acquisitions through a sequence of illuminating projections. When reconstructed, the images may provide high resolution data that may establish length, width, and/or depth information. The phase information may establish a refractive index and/or optical thickness of an object or sample. The data captured may be retained within a local or a remote memory or database that facilitates real-time imaging and viewing (e.g., through a display) locally or at a remote site. The speed that images captured may depend on the frame rate of capture of an interfaced recording device or latency in which the data is stored or written into the local and/or remote memory. The magnification may differ from some phase-shifting techniques, in which the speed of image capture may depend on the speed at which the phase-shifting device may be adjusted.

Tomographic characteristics recorded in a computer readable media by the optical system may provide information about internal structures within the object without invading the object or applying invasive techniques. Some optical systems may capture two dimensional images of the object over a range between about zero and about one-hundred and twenty degrees. Alternative optical systems may capture images from illuminating projections that may range between about zero and less than about one-hundred and eighty degrees. The optical systems capture data that render three-dimensional structures in real-time. The angular spacing between illuminating projections may determine (in part) the quality and resolution of the length, width, and/or depth (e.g., three dimensions) of a reconstructed image. When smaller angles (increased angular sampling) are processed, a high resolution image in three dimensions may be generated.

By eliminating or avoiding a phase shift of about $\pi/2$ over a range of illumination angles, some optical systems do not need to capture multiple images (or shots) at each projection angle to render three dimensional data of a quantitative refractive index. By limiting or eliminating a continuous writing to non-volatile (or volatile) memory that retains data as part of a local or remote database, acquisition times are reduced and temporal resolution is improved. The improved resolution enhances distinctness and image clarity of live dynamic events or organisms. It may also reduce the delay of executing software-based algorithms that may derive absolute phase data.

In some systems a digital optical interferometer device may reveal the internal structures within the specimen by performing an object beam rotation over a specified or pre-programmed angular arc. The data may be written to a local or remote memory at high speeds as a single digital image is captured at each illuminating projection angle through the object or sample. This single-shot capability at each angularity reduces the image acquisition time.

The intensity and phase information of the optical system that includes a digital optical interferometer device may be simultaneously (or nearly simultaneously) reconstructed from a stored or recorded complex wave-front in high-speed (e.g., at the same rate the data is received), allowing some optical systems to function as a bright-field and quantitative three-dimensional phase-contrast microscope in real-time. The information in the phase image may be determined by a thickness/refractive index variations (in some optical systems exclusively) that allow the object (e.g., living biological cells) to be observed without staining. The optical interferometer device may be numerically focused to emulate focus controls of other magnifying devices but with higher resolution. Because focusing may be adjusted in a reconstruction process, a digital optical interferometer device may be free of the limitations of a mechanical focused system. This feature may allow the optical system to monitor a sample's dynamics irrespective of depth variations.

To specify detailed information that identifies individual structures, the optical systems may include an excitation-emission device (or epi-fluorescence devices in alternate optical systems). The excitation-emission device may generate emissions (or florescence in some optical systems) by reflection (rather than transmitted light) to magnify the functional details of a sample. The excitation-emission magnification may occur on a discrete schedule (e.g., enabling the excitation-emission and optical interferometer devices in sequence or series), interactively, in real time and/or continuously with one or more digital optical interferometer magnifications or devices.

In some applications, the correlation between the transmissive and reflective magnifications may be processed to analyze the relationship between cellular structures and function through a local or remote signal processor, computer, or server. To obtain quantitative phase data, some optical systems include one or more multiple-wavelength digital optical interferometers (or holographic devices in some alternate systems). Multiple wavelengths may provide a deterministic method to obtain phase data beyond a characteristic ambiguity limit. Some optical systems eliminate time consuming phase unwrapping algorithms or processes that may be prone to errors. By performing imaging in a transmissive and a reflective mode (separately or synchronously), the optical system may obtain quantitative phase data both deterministically and with high speed. The optical system may capture a large depth of field in a single image (e.g., a single shot), provide numerical focusing that renders distinctness and image clarity, and the correction of optical aberrations in real-time with a non-invasive system.

In some optical systems increasing the phase range (optical phase unwrapping) may be implemented through two or more wavelengths. The combination of phase images of two different wavelengths $\lambda_1$ and $\lambda_2$ in an alternative optical system may render another phase image having an effective wavelength (or synthetic wavelength) described by equation 1.

$$\Lambda_{12}=\lambda_1\lambda_2/|\lambda_1-\lambda_2|. \quad (1)$$

At an effective wavelength, the measured phase is measured longer than either of the two probing wavelengths. This approach may eliminate the problems of mathematical phase unwrapping algorithms. The process is deterministic, does not have problems with certain mapping or image topologies, and may be processed at times that may measure about a fraction of a second.

To obtain a longer measurement range, the two wavelength values $\lambda_1$ and $\lambda_2$ (from equation 1) may be selected close together. When the difference between the two images is taken from wavelengths that are far apart, some synthetic wavelengths, $\Lambda_{12}$, may become noisy due to amplification error. This effect may be minimized or substantially overcome in alternate optical systems that include three or more wavelength digital optical interferometer or holographic devices. These devices (or controllers in communication with them) may use hierarchical synthetic-wavelength reduction processes to render a magnified image. The use of three or more wavelength digital optical interferometers or holographic devices may facilitate longer range measurements without increasing the phase noise. As the multiple-wavelength wave-front may be captured in real-time, the alternate system may make direct, long-range shape measurements of dynamically moving samples in high resolution in real-time or at an improved speed.

FIG. 1 is a single wavelength optical system 100 (that includes an interferometer) that may perform imaging in a transmissive or reflective mode. An object and reference beams 104 and 106 are created along two separate and well-defined optical paths using a fiber optic delivery system. The object beam 104 and reference beams 106 originate from a light source 108 that transmits an electromagnetic spectrum in a visible or an invisible range to a common input of a 1×2 fiber optic coupler 110.

In some alternative optical systems that combine phase contrast and emission systems images (e.g., synchronize transmissive and reflective magnifications), an optional optical shutter (e.g., a high speed optical shutter that is not shown) movable or rotatable through the object path may control the frequency and duration of exposure of the (object or) sample 112 to the object beam 104 by rotating one or more lenses through the object path. The optional optical shutter may be positioned between the fiber optic coupler 110 and a scanner 114 (e.g., an open or closed loop galvanometer scanner) or between the scanner 114 (or each of the scanners in multiple scanning systems) and the microscope objective 116. The optical shutter may be synchronized to a Charge Coupled Device (CCD) such as a two dimensional or CCD camera 118 through a digital delay generator (DDG) or controller (not shown). In some optical systems, the DDG or controller utilizes or communicates with a non-volatile (e.g., flash memory) or volatile memory to execute programmable sequences and delays. This synchronization allows the quantitative phase and emissions (e.g., fluorescence information) to be obtained synchronously or concurrently with the interference phenomena.

Figure 4:
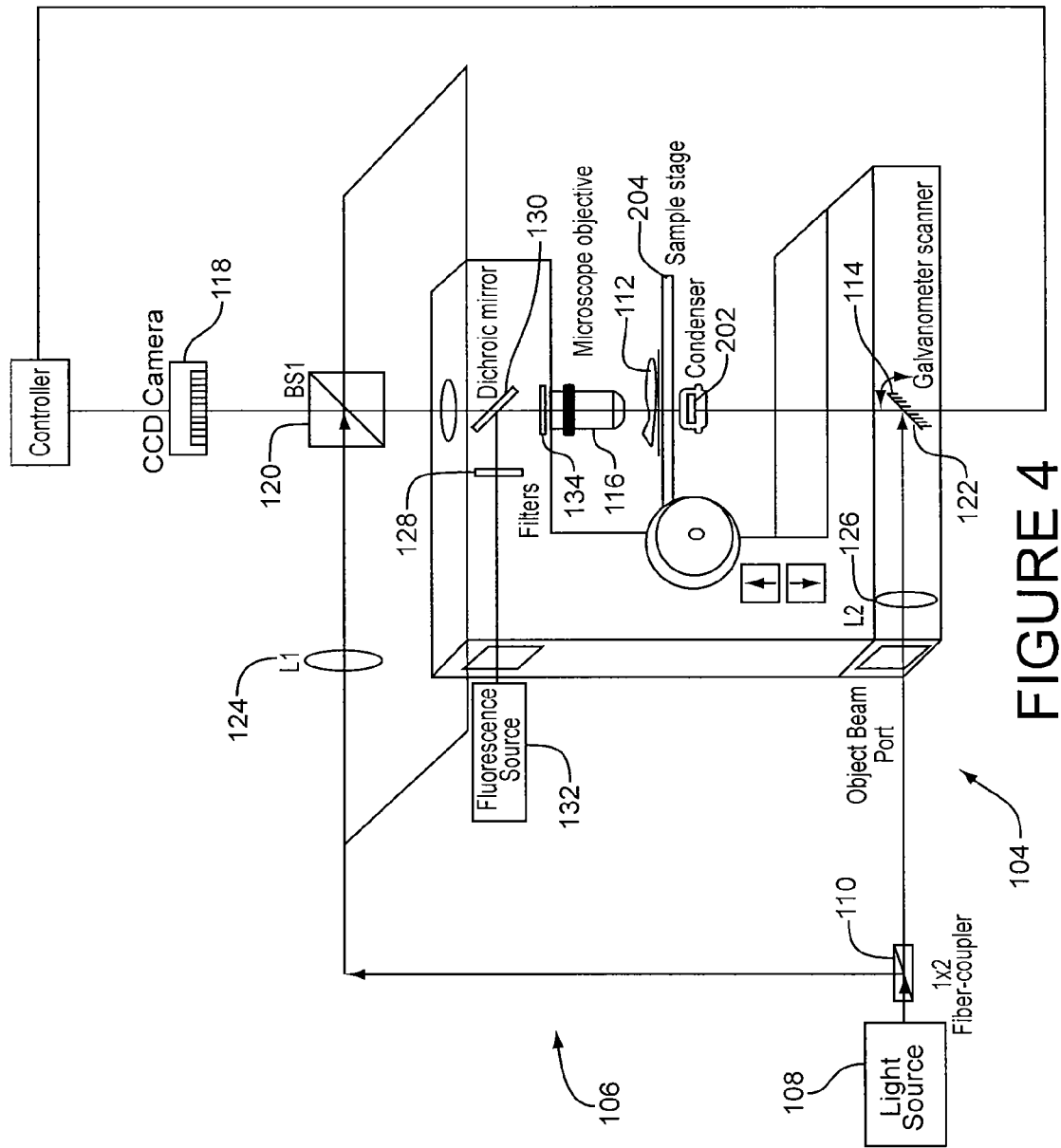
FIG. 4 is a single wavelength optical interferometer and excitation-emission device of FIG. 1 in communication with a controller.

An object beam illumination may be scanned through two, three, or more angled illumination projections through the (object or) sample 112. A scanner 114 (an open or closed loop galvanometer) may facilitate motion to one or more deflecting surfaces (or mirrors) 122 that receive collimated light from a second lens 126. Some scanners 114 are driven by a rotary motor that moves the deflecting surface 122 through angularities established by a processor and the commands written to and read from a local or a remote memory. A high-precision position detector (such as a high resolution rotary encoder of a closed loop galvanometer) may transmit control signals to the processor to track angular position, and in some applications, render angular velocity. An optional temperature detector may monitor variations in ambient temperature or variations in deflecting surface 122 temperatures to ensure that the processor commands precise deflections. At each illumination angle along a single axis (or in alternative systems, dual axis), an interference phenomena between the object beams and the reference beams 104 and 106 that occurs in the beam splitter 120 (e.g., filter cube) may be captured by a Charge-Coupled-Device (CCD) like a CCD camera 118. In FIG. 1, the transmitted light of the reference beam 104 is focused and coupled to the beam splitter 120 by a first lens 124. The CCD (e.g., CCD camera 118) may record the outputs (or holograms) of the digital optical interferometer before it is digitally transferred to a local or remote controller through a wireless or tangible link to a local or remote controller as shown in FIG. 4. The quantitative amplitude and phase of each complex wave-front may then be extracted and processed.

Off-axis digital interference phenomena (or holograms) are created by deflecting the reference illumination angle with respect to the object beam 104. The tilt may create a frequency modulation in the interference phenomena (or holograms) created between the object and the reference beams 104 and 106 that renders a separation in the interference (or holographic) terms and the DC term in a Fourier space.

To excite the excitation elements within (or florescence within) the species in the sample (or object) 112, a high intensity light source 132 (or florescence source) such as a mercury lamp, for example, may illuminate the sample (or object) 112. Optics within the excitation-emission device (or epi-fluorescence device) separate the illumination (or excitation) light from the emission that emanates from the sample (or object) 112 that passes through the microscope objective 116. To select the proper excitation wavelength, an excitation filter 128 is disposed in the excitation path between a dichroic mirror 130 (or beam splitter) and the excitation light source 132. A wavelength selective device, such as an emission filter 134 selects the emission wavelengths of the electromagnetic spectrum emitted from the sample (or object) 112. The wavelength selective device may be placed between the dichroic mirror 130 and the CCD 118 to select the emission wavelength and eliminate nearly any or substantially all of the wavelengths used for excitation.

In an alternative optical system, a common path interferometer may process the interference phenomena between the object and reference beams 104 and 106 to measure wavelengths, wave velocities, distances, sample 112 (or object) thickness, and/or measure indices of refraction. In this alternative optical system, the object and reference beams 104 and 106 propagate through a common optical path. A grating provides frequency modulation and may separate interference (or holographic) terms and the DC term in the Fourier space.

In each optical system, successive or interrupted interference (or holographic) projections may be captured and stored in the local or remote memory with a reference or pointer to each corresponding angle (e.g., sonogram when an inverse Radon transform is performed) in the memory or other storage device. Three dimensional data of inner structures may be reconstructed through the inverse Radon transform, filtered back-projections, or other processes. In some exemplary applications where a scanning orbit is limited to a predetermined angularity (<180-degrees) and/or large angular spacing between interference (or holographic) projections is restricted (e.g., limited to a pre-programmed angular separation), a model-based iterative reconstruction approach generates a clear, less noisy three dimensional magnified image.

Figure 2:
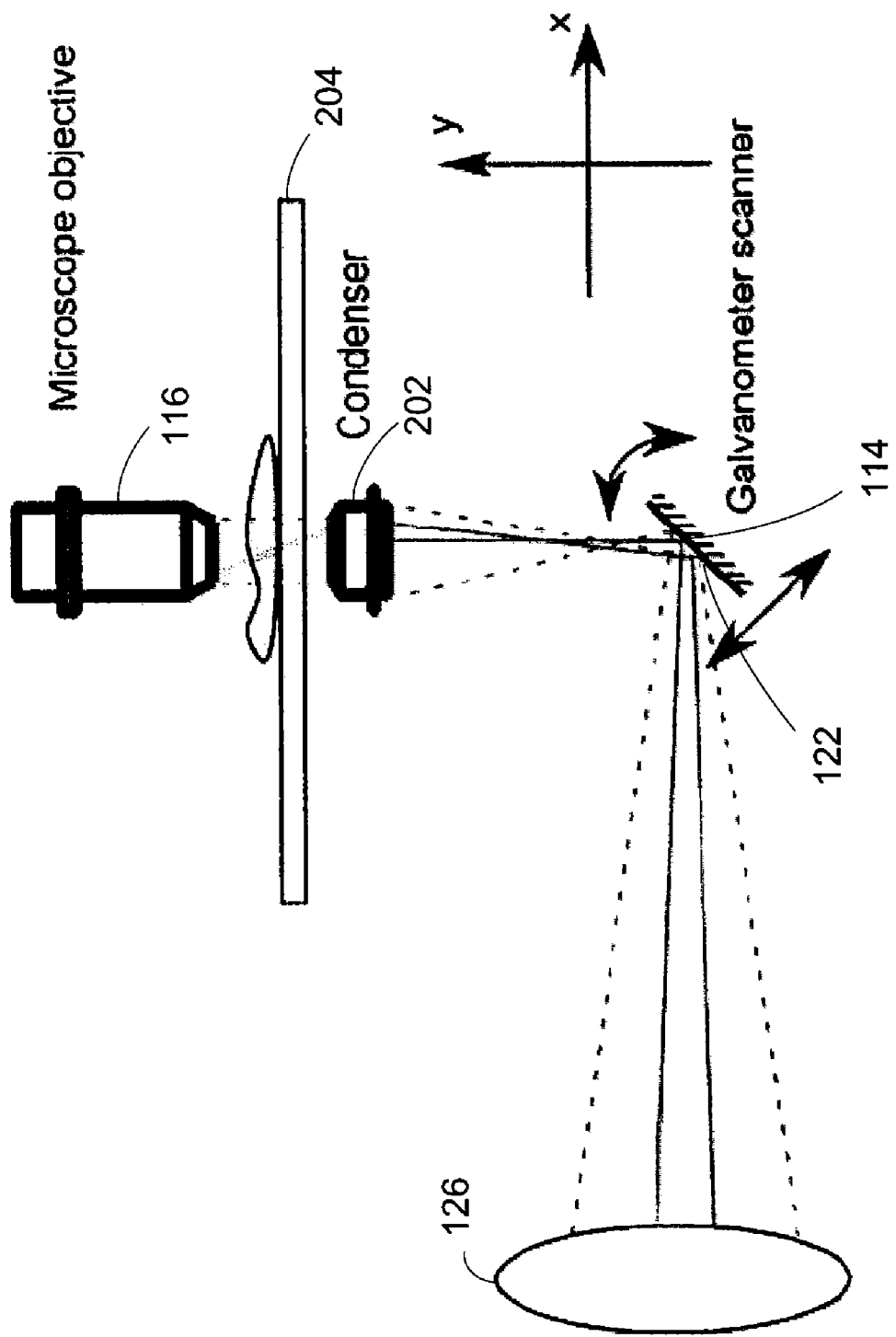
FIG. 2 is a tomographic illumination through an object.

Another alternative optical system provides fast accurate scanning through a dual axis deflection (e.g., use a dual axis galvanometer). By adding a second tilt axis to the deflecting surface 122 (or mirror) multiple sets of interference (or holographic) projections may be captured and stored in memory. In FIG. 2, two or more axis (two are shown x, y, but three or more axis are used in alternate systems) of rotation of the deflecting surface 122 (or mirror) may deflect the collimated light transmitted from the second lens 126. A mirror, lens, or a combination of lenses (e.g., a condenser) 202 gathers the light 204 and directs it upon the (object) or sample 112 through a projection lens or aperture within a sample stage 204. Additional axis of deflection allows alternative optical systems to acquire more views before reconstructing a (single) three dimensional single image from a volume of data associated with an arc or angularities. When reconstructed, the resulting combined volumes may render clearer three dimensional or topographic images or a sequence of images that may be rendered through a display with sufficient rapidity to create motion or continuity (e.g., video) or the illusion of motion and continuity with reduced noise. Similar sequences may be generated in each of the optical systems disclosed herein.

Some other alternative optical systems may provide multiple axis of deflection through two or more light sources, mirrors, scanners (e.g., galvanometer sets). In a dual axis application, for example, one scanner (or galvanometer) may have a range of motion along the X-axis, and the other scanner (or galvanometer) may have a range of motion along the Y-axis. In this configuration, some alternative optical systems collect, deflect, and direct light from separate light sources in a substantially horizontal and a substantially vertical direction, respectively. Using an inverse Radon transform process, or a model-based, iterative reconstruction process (e.g., expectation maximization), or another process or combination retained in a computer readable storage medium, a processor may reconstruct magnified images in two and/or three dimensions that may be projected at a sufficient speed to capture the motion and continuity occurring in the sample in real-time (See FIG. 4).

Figure 3:
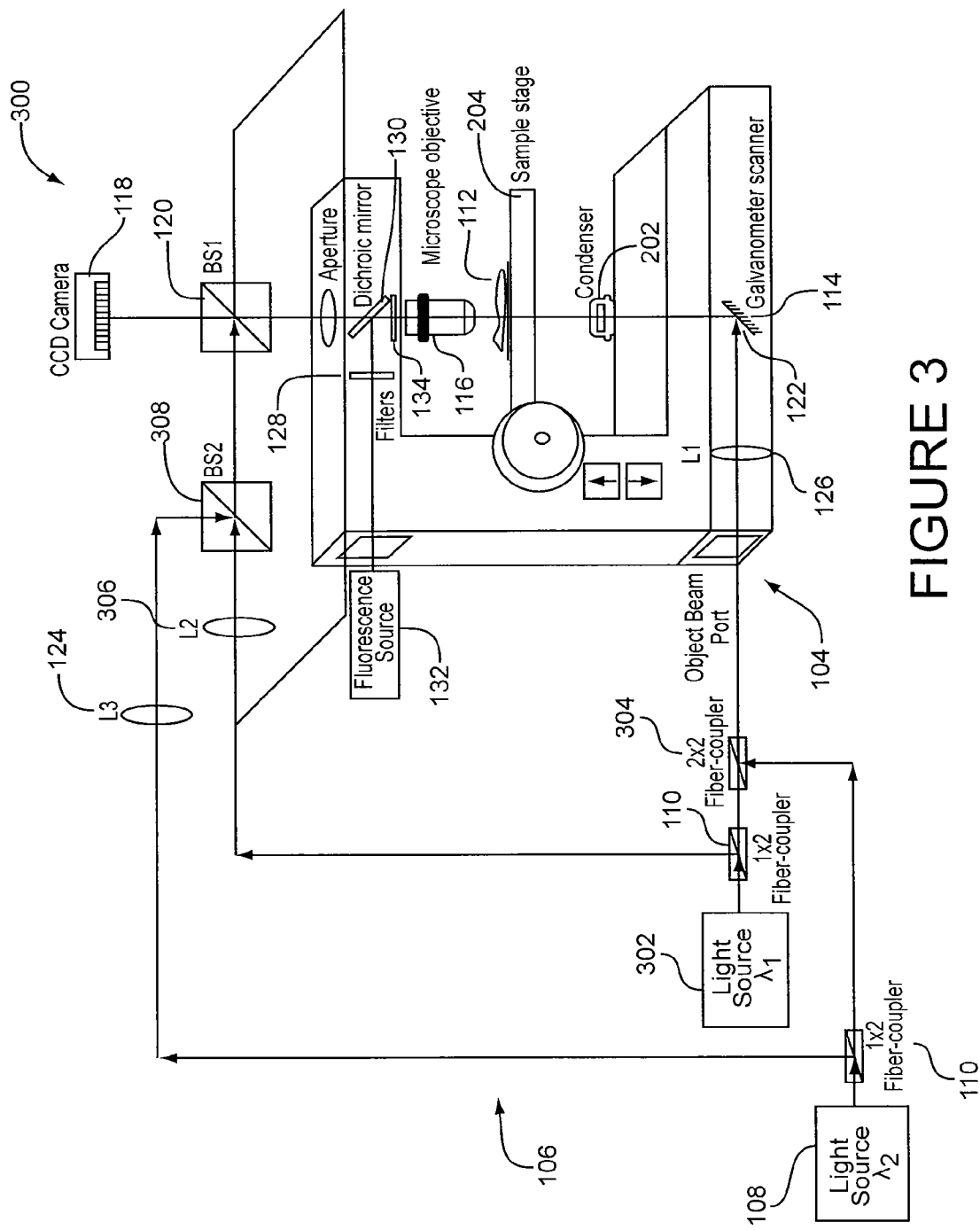
FIG. 3 is a multiple wavelength optical interferometer and excitation-emission device.

FIG. 3 shows a two wavelength optical system 300 that includes two interferometers in an achromatic arrangement that brings two wavelengths emitted from two light sources into one imaging optical system. The reference beams 106 of each (holographic device or) interferometer may be adjusted so that the two holograms (or two interference phenomena) may be recorded or written to memory at each angularity (or illuminating projection) through a single digital image (at each angularity) that captures separate sets of spatial frequencies. The optical system 300 may capture multiple-wavelengths of a complex wave-front at each illuminating angle in real-time.

In the arrangement of FIG. 3, the reference beams originate from two (e.g., multiple) separate light sources 108 and 302 that have electromagnetic spectrums in the visible or invisible electromagnetic range. Fiber optic coupler 110 having three or more fiber optic ends split the input fiber optic light into two or more parts to the outputs (e.g., the object path and the reference path) at a predetermined ratio. The fiber optic coupler 110 may interface a single mode fiber optic cable and may comprise a single window. A single window may have a single wavelength with a narrow wavelength window. A multiple window fiber optic coupler (not shown) may support two or more wavelengths in alternate systems with a wide wavelength window for each input.

A fiber optic coupler 304 combines the object beams in the object path. The transmitted light of the reference beams are focused and coupled to a filter cube 308 that combines and directs the composite reference beam to the beam splitter 120.

In some alternative optical systems that combine phase contrast and emission systems images (e.g., synchronize transmissive and reflective magnifications), an optional optical shutter (e.g., a high speed optical shutter that is not shown) movable or rotatable through the individual or composite object path may control the frequency and duration of exposure of the (object or) sample 112 to the object beam 104 by rotating one or more lenses through the object path. The optional optical shutter may be positioned between the fiber optic coupler 304 and the scanner 114 (e.g., an open or closed loop galvanometer scanner) or between the scanner 114 (or each of the scanners in multiple scanning optical systems) and the microscope objective 116. The optical shutter may be synchronized to the Charge Coupled Device (CCD) such as the CCD camera 118 through a digital delay generator (DDG) or controller (not shown). In some optical systems, the DDG or controller utilizes or communicates with a non-volatile (e.g., flash memory) or volatile memory to execute programmable sequences and delays. This synchronization allows the quantitative phase and emissions (e.g., fluorescence information) to be obtained synchronously or concurrently (e.g., in real-time) with the interference phenomena.

When the interference phenomena or holograms have been captured through a CCD device or camera 118, the images at each angularity and excitation-emission images or volume of images may be transmitted through a parallel or serial interface (e.g. an IEEE 1394b) and a wireless or tangible medium to a remote or local processor or signal processor. Numerical band-pass filters (devices or programs) may process the separate interference or holographic terms originating from the multiple wavelengths, from which the interference or holographic phase images may be reconstructed. Through the numerical focusing of the digital interferometers or holographic devices, the reconstructed images at each wavelength and angularity may be focused to enable an exact (or nearly exact superposition) of the sample 112. When three different lights sources (or more) are used in an alternate optical system (e.g., three or more optical interferometers), the alternate optical system may further enhance the measurement capability, allowing for long range phase imaging while maintaining the high-precision of the measurement.

In some optical systems, communication may occur through a wireless protocol. The communication protocol may provide an interoperable communication link with CCD and sensors, DDG devices, external applications, processors and/or remote sites. In some systems, the wireless links provides connectivity when the wireless network or a wireless service provider indicates a channel capacity or excess channel capacity to transfer some or all of the desired data to a destination. A CCD device may push desired data to a destination and may keep a connection open to allow the CCD device, sensors, DDG device, controllers, and/or etc. (CCD et al.), to continue to send desired data or respond to external requests (e.g., queries) as a sample is monitored (e.g., in real-time). A CCD et al. may pull data from a site in real-time too through a persistent or non-persistent connection.

Each of the systems described (or to be described) may include a wireless transceiver compliant with a cellular or wireless protocol, a wireless or cellular telephone, a radio, a satellite, or other wireless communication system that may link the CCD et al to a privately accessible or publicly accessible distributed network or directly to an intermediate surrogate or central operations center. The communication link may comprise Mobile-FI or a low-cost, always-on, mobile broadband wireless network that may have IP (Internet Protocol) roaming & handoff (at more than about 1 Mbit/s), MAC and PHY with IP and adaptive antennas, full mobility or substantial mobility up to vehicle speeds of about 88.7-162 km/h or higher (e.g., 250 km/h), operate in frequency bands (below 3.5 GHz), and/or utilize a packet architecture and have a low latency.

In some applications, the optical system may be Ultrawideband compliant and may transmit information by generating radio energy at specific time instants and occupying large bandwidth, thus enabling a pulse-position or time-modulation communications. This protocol may be different from other wireless protocols that transmit information by varying the power level, frequency, and/or phase of a sinusoidal wave.

In other applications, the optical device may be complaint with WiMax or IEEE 802.16a or may have a frequency band within a range of about 2 to about 11 GHz, a range of about 31 miles, and a data transfer rate of about 70 Mbps. In other applications, the mobile monitoring device 100 may be compliant with a Wi-Fi protocols or multiple protocols or subsets (e.g., ZigBee, High Speed Packet Access (e.g., High Speed Downlink Packet Access and/or High Speed Uplink Packet Access), Bluetooth, Mobile-Fi, Ultrawideband, Wi-Fi, WiMax, mobile WiMax, cellular, satellite, etc., referred to as the transceiver protocols) that may be automatically detected and selected (through a handshaking, for example, that may automatically determine the source type of the transmission e.g., by a query for example, and may attempt to match it) and may enable this automatic access through one or more communication nodes.

To excite the florescent species in the sample of FIG. 3, a high intensity light source 132 such as a mercury lamp, for example, may illuminate the sample. Optics within an exemplary epi-fluorescence (or excitation-emission) device separate the illumination (or excitation) light from the (florescence) emission that emanates from the sample that passes through the microscope objective 116. To select the proper excitation wavelength, an excitation filter 128 is disposed in the excitation path between the high intensity light source 132 and the dichroic mirror 130. A wavelength selective device, such as an emission filter 134 selects the emission wavelengths of light emitted from the sample 112. The wavelength selective device may be placed between the microscopic objective 116 and the CCD 118 to select the emission wavelength and eliminate nearly any or substantially all of the wavelengths used for excitation. When transmissive and reflective magnifications are combined, the (fluorescence) data is separated from the interferometer (or holographic) data by the optional high-speed shutter (that may be driven by a closed loop servomotor monitored by a rotary encoder) and an optional DDG.

Another alternative optical system of FIG. 3 provides fast accurate scanning through a dual axis deflection (e.g., use a dual axis galvanometer). By adding a second tilt axis to the deflecting surface 122 (or mirror), multiple sets of interference (or holographic) projections may be captured and stored in memory. In FIG. 3, two or more axis (in an x and y direction or three or more axis may mechanically translate deflecting surfaces in alternate optical systems) of rotation of the deflecting surface 122 (or mirror) may deflect the collimated light transmitted from the second lens 126. A mirror, lens, or a combination of lenses (e.g., a condenser) 202 gathers the light 104 and directs it upon the (object) or sample 112 through a projection lens or aperture within a sample stage 204. Additional axis of deflection allows alternative optical systems to acquire more views before reconstructing a (single) three dimensional single image from a volume of data associated with an arc or angularities. When reconstructed, the combined volumes of images (e.g., images at each angularity) may render clearer three dimensional or topographic images or a sequence of images that may be rendered by a display with sufficient fluidity to create motion or continuity or the illusion of motion and continuity with reduced noise. Similar sequences may be generated in each of the optical systems disclosed.

Figure 5:
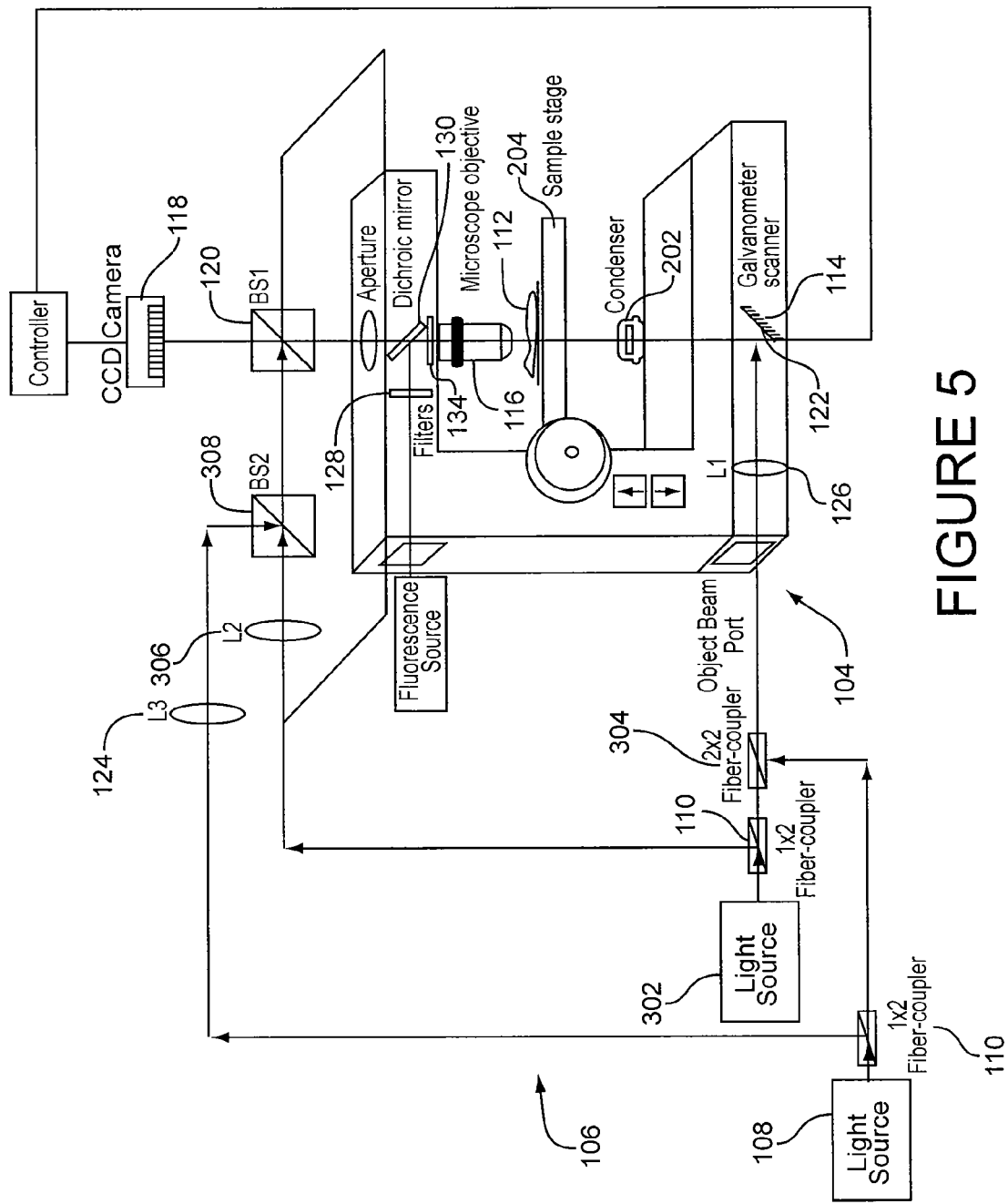
FIG. 5 is the multiple wavelength optical interferometer and excitation-emission device in communication with a controller.

Another alternative optical system of FIG. 3 may provide multiple axis of deflection through two or more light sources, mirrors, scanners (e.g., galvanometer sets). In a dual axis application, for example, one scanner (or galvanometer) may have a range of motion along the X-axis, and the other scanner (or galvanometer) may have a range of motion along the Y-axis. In this configuration, some alternative optical systems collect, deflect, and direct light from separate light sources in a substantially horizontal and a substantially vertical direction, respectively. Using an inverse Radon transform process, or a model-based, iterative reconstruction process (e.g., expectation maximization), or another process or combination retained in a computer readable storage medium, a processor may reconstruct magnified images in two and/or three dimensions that may be projected at a sufficient speed to capture the motion and continuity occurring in the sample in time (See FIG. 5).

In each of the systems described (or to be described), an optional visual output device or display that may interface the local or remote memory, a remote or local processor, the CCD et al., etc. The display may support a graphical user interface that may allow an operator to enter point of interest identifiers (through icons, menus, dialog boxes, etc. selected through absolute and/or relative pointing devices) so that recorded characteristics may be associated with an image, map, (e.g., a topological map or simplified map that lacks some details or a topographic map that may show many details through contour lines, models, or other visual representations, or etc., for example) or combination thereof. Some graphical user interfaces interface a touch screen that recognizes location and the intensity of touch (or simultaneous touches) on its surface by an operator or input device.

Some or all of optical systems may communicate with an optional visual output that may comprise a Light Emitting Diode display (LED), a Liquid Crystal display (LCD), or a remote controller (e.g., a computer screen, portable computer, a tablet computer, a personal digital device, and/or other displays) wirelessly or tangibly linked to the optical system. In some systems, the display may render real-time or delayed audio, visual, and/or tactile representations when a condition is detected, completed, is measured, or a programmed event occurs, etc.

Other alternate systems and methods may include combinations of some or all of the structure and functions described above or shown in one or more or each of the figures. These systems or methods are formed from any combination of structure and function described or illustrated within the figures.

The methods and descriptions herein may be programmed in one or more controllers, devices, processors (e.g., signal processors). The processors may comprise one or more central processing units that supervise the sequence of microoperations that execute the instruction code and data coming from memory (e.g., computer memory) that generate, support, and/or complete a compression or signal modifications. The dedicated applications may support and define the functions of the special purpose processor or general purpose processor that is customized by instruction code (and in some applications may be resident to vehicles). In some systems, a front-end processor may perform the complementary tasks of gathering data for a processor or program to work with, and for making the data and results available to other processors, controllers, or devices.

The methods and descriptions may also be programmed between one or more signal processors or may be encoded in a signal bearing storage medium a computer-readable medium, or may comprise logic stored in a memory that may be accessible through an interface and is executable by one or more processors. Some signal-bearing storage medium or computer-readable medium comprise a memory that is unitary or separate from a device, programmed within a device, such as one or more integrated circuits, or retained in memory and/or processed by a controller or a computer. If the descriptions or methods are performed by software, the software or logic may reside in a memory resident to or interfaced to one or more processors or controllers that may support a tangible or visual communication interface, wireless communication interface, or a wireless system.

The memory may include an ordered listing of executable instructions for implementing logical functions. A logical function may be implemented through digital circuitry, through source code, or through analog circuitry. The software may be embodied in any computer-readable medium or signal-bearing medium, for use by, or in connection with, an instruction executable system, apparatus, and device, resident to system that may maintain persistent or non-persistent connections. Such a system may include a computer-based system, a processor-containing system, or another system that includes an input and output interface that may communicate with a publicly accessible distributed network through a wireless or tangible communication bus through a public and/or proprietary protocol.

A "computer-readable storage medium," "machine-readable medium," "propagated-signal" medium, and/or "signal-bearing medium" may comprise any medium that contains stores, communicates, propagates, or transports software or data for use by or in connection with an instruction executable system, apparatus, or device. The machine-readable medium may selectively be, but not limited to, an electronic, magnetic, optical, electromagnetic, infrared, or semiconductor system, apparatus, device, or propagation medium. A non-exhaustive list of examples of a machine-readable medium would include: an electrical connection having one or more wires, a portable magnetic or optical disk, a volatile memory, such as a Random Access Memory (RAM), a Read-Only Memory (ROM), an Erasable Programmable Read-Only Memory (EPROM or Flash memory), or an optical fiber. A machine-readable medium may also include a tangible medium upon which software is printed, as the software may be electronically stored as an image or in another format (e.g., through an optical scan), then compiled, and/or interpreted or otherwise processed. The processed medium may then be stored in a computer and/or machine memory.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

What is claimed is:
1. An optical system that performs imaging in a transmissive and reflective mode comprising:
   an optical interferometer configured to generate an interference phenomena between optical waves to measure a plurality of distances, a plurality of thicknesses, and a plurality of indices of refraction of a sample;

an excitation-emission device in which an electromagnetic excitation and emission pass through an objective in optical communication with the sample; and an electromagnetic detector configured to receive an output of the optical interferometer and the excitation-emission device to render a magnified image of at least a portion of the sample;

where the optical interferometer includes a closed loop galvanometer that scans a pre-programmed angular arc to render a three-dimensional view of the portion of the sample;

where the optical interferometer comprises a coupler with an input, an object beam output, and a reference beam output; and where the closed loop galvanometer is coupled between the object beam output of the coupler and the objective.

2. The optical system of claim 1 further comprising:

a digital delay generator that synchronizes the optical interferometer and the excitation-emission device to operate substantially in unison, where the digital delay generator is configured to generate a noninvasive depth of field of the portion of the sample, and where the digital delay generator is configured to correct a plurality of optical aberrations in real-time; and a wireless transceiver in communication with the digital delay generator that transmits the output of the optical interferometer and excitation-emission device at the same rate as the data is received.

3. The optical system of claim 2 where the optical interferometer and excitation-emission device are further synchronized by an optical shutter.

4. The optical system of claim 2 where the optical interferometer and excitation-emission device are further synchronized by a plurality of wavelength selective devices.

5. The optical system of claim 2 where the optical interferometer and excitation-emission device are further synchronized by a plurality of charge coupled device sensors.

6. The optical system of claim 2 where the digital delay generator is in communication with a non-volatile memory that stores programmable sequences that synchronizes the optical interferometer and the excitation-emission device to obtain a qualitative phase and emission data of the portion of the sample substantially simultaneously.

7. The optical system of claim 2 where optical interferometer generates a plurality of interference phenomena that renders a plurality of images of the portion of the sample substantially simultaneously.

8. The optical system of claim 1 where the optical interferometer generates at least two images.

9. The optical system of claim 1 where the closed loop galvanometer has a range of motion along a dual axis.

10. The optical system of claim 1 where the closed loop galvanometer comprise a plurality of closed loop galvanometers each having a range of motion along a dual axis.

11. The optical system of claim 1 where the closed loop galvanometer comprise a plurality of closed loop galvanometers each having a range of motion along a single axis.

12. The optical system of claim 1 where the optical interferometer comprises a plurality of holographic devices that generate more than one hologram that is written to a memory through a single image at each angularity the closed loop galvanometer rotates about a predetermined arc.

13. The optical system of claim 1 where the optical interferometer comprises a common path interferometer in which a beam and a reference beam propagate through a common path and a grating generates a frequency modulation that separate interference terms.

14. The optical system of claim 1 further comprising a computer readable storage media accessible to the electromagnetic detector that stores reconstruction code that renders a three-dimensional image of the portion of the sample.

15. The optical system of claim 14 further comprising a rotary encoder that generates positional feedback of the closed loop galvanometer transmitted to a local controller.

16. The optical system of claim 1 further comprising a publicly accessible network that enables remote users to access real-time magnified three-dimensional images of the sample generated from the integration of the output of two or more optical interferometers from a remote site.

17. The optical system of claim 1 further comprising a privately accessible network that enables remote users to access real-time magnified full-field view of the sample generated from the integration of the output of two or more optical interferometers from a remote site.

18. An optical system that performs imaging in a transmissive and reflective mode comprising:

a plurality of optical interferometers that generates an interference phenomena between optical waves to measure a plurality of distances, a plurality of thicknesses, and a plurality of indices of refraction of at least a portion of a sample;

an excitation-emission device in which an electromagnetic excitation and emission pass through an objective in optical communication with at least the portion of the sample;

an electromagnetic detector that receives an output of at least one of the plurality of optical interferometers and the excitation-emission device to render a magnified image of at least the portion of the sample;

a digital delay generator that synchronizes at least one of the plurality of optical interferometers and the excitation-emission device to operate in substantial unison to generate a noninvasive depth of field of the portion of the sample in real-time;

a galvanometer that scans a pre-programmed angular arc to render a three-dimensional view of the portion of the sample;

a display that renders a magnified topographic image of at least the portion of the sample in real time; and an interferometer coupler configured to split an input optical signal into an object beam output and a reference beam output before passing the object beam output to the galvanometer.

19. The optical system of claim 1 further comprising a graphical user interface programmed to allow an operator to enter point of interest identifiers that record characteristics associated with the topographic image.

20. An optical system that performs imaging in a transmissive and reflective mode comprising:

a plurality of optical interferometers configured to generate an interference phenomena between optical waves to measure a plurality of distances, a plurality of thicknesses, and a plurality of indices of refraction of at least a portion of a sample;

an excitation-emission device in which an electromagnetic excitation and emission pass through an objective in optical communication with at least the portion of the sample;

an electromagnetic detector configured to receive an output of at least one of the plurality of optical interferometers and the excitation-emission device to render a magnified image of at least the portion of the sample;

a closed loop galvanometer configured to scan a pre-programmed angular arc to render a three-dimensional view of the portion of the sample;

an interferometer coupler that includes an input, an object beam output, and a reference beam output, where the closed loop galvanometer is coupled between the object beam output of the coupler and the objective; and a display that renders a magnified image of at least the portion of the sample in real time, where the electromagnetic detector comprises a monochrome charge coupled device that stores a portion of the output of the at least one of the plurality of optical interferometers and a portion of the output of the excitation-emission device in a memory.

21. The optical system of claim 1 further comprising:

a position detector associated with the closed loop galvanometer;

a processor in communication with the position detector, where the position detector and the processor are configured to track an angular position of the closed loop galvanometer; and a rotary motor configured to move a deflecting surface of the closed loop galvanometer through angularities established by the processor.

22. The optical system of claim 1 where the coupler is configured to split an input optical signal into an object beam and a reference beam before passing the object beam to the closed loop galvanometer.

23. The optical system of claim 18 where the galvanometer comprises a closed loop galvanometer.

* * * * *